United States Patent [19]
Sin et al.

[11] Patent Number: 6,150,174
[45] Date of Patent: Nov. 21, 2000

[54] METHOD FOR MEASUREMENT OF WHOLE BLOOD COAGULATION PARAMETERS

[75] Inventors: Kee Van Sin, Lino Lakes; Carter R. Anderson, Eagan, both of Minn.

[73] Assignee: Diametrics Medical, Inc., St. Paul, Minn.

[21] Appl. No.: 09/034,478

[22] Filed: Mar. 4, 1998

Related U.S. Application Data

[60] Provisional application No. 60/038,593, Mar. 5, 1997.

[51] Int. Cl.⁷ .................................................. G01N 33/86
[52] U.S. Cl. .............................. 436/69; 436/70; 436/164; 422/73; 422/82.05; 422/82.09; 73/64.41; 73/64.43; 600/369
[58] Field of Search .................. 436/63, 69, 70, 436/149, 150, 164, 165; 422/68.1, 73, 82.01, 82.02, 82.05, 82.09; 435/2, 13; 73/64.41, 64.43; 600/369

[56] References Cited

U.S. PATENT DOCUMENTS

| | | | |
|---|---|---|---|
| 3,699,437 | 10/1972 | Ur | 324/722 |
| 3,840,806 | 10/1974 | Stoner et al. | 324/722 |
| 4,252,536 | 2/1981 | Kishimoto et al. | 356/36 |
| 4,319,194 | 3/1982 | Cardinal et al. | 324/449 |
| 4,547,735 | 10/1985 | Kiesewetter et al. | 464/32 |
| 4,640,896 | 2/1987 | Farrell et al. | 436/34 |
| 4,659,550 | 4/1987 | Schildknecht | 422/73 |
| 4,756,884 | 7/1988 | Hillman et al. | 422/73 |
| 4,849,340 | 7/1989 | Oberhardt | 435/13 |
| 4,876,069 | 10/1989 | Jochimsen | 422/73 |
| 5,167,145 | 12/1992 | Butler et al. | 73/64.43 |
| 5,298,224 | 3/1994 | Plum | 422/73 |
| 5,346,604 | 9/1994 | Van Sin et al. | 204/415 |
| 5,385,846 | 1/1995 | Kuhn et al. | 436/70 |
| 5,401,663 | 3/1995 | Yonemura | 436/69 |
| 5,418,141 | 5/1995 | Zweig et al. | 435/13 |
| 5,447,440 | 9/1995 | Davis et al. | 435/6 |
| 5,580,744 | 12/1996 | Zweig | 435/13 |
| 5,601,995 | 2/1997 | Exner | 435/13 |
| 5,827,746 | 10/1998 | Duic | 436/70 |

FOREIGN PATENT DOCUMENTS

| | | |
|---|---|---|
| 0582431 | 7/1993 | European Pat. Off. . |
| 1239589 | 11/1984 | U.S.S.R. . |
| 1503014 | 11/1984 | U.S.S.R. . |

*Primary Examiner*—Maureen M. Wallenhorst
*Attorney, Agent, or Firm*—Dorsey & Whitney LLP

[57] ABSTRACT

The present invention provides a method for determining the coagulation propensity of blood wherein a condition in a portion of a blood sample is assessed and related to the onset of coagulation. Apparatus for performing the method is encompassed by the invention.

4 Claims, 7 Drawing Sheets

TIME 1  TIME 2  TIME 3

TIME 1

TIME 2

TIME 3

METHOD FOR MEASUREMENT OF WHOLE BLOOD COAGULATION PARAMETERS

This application claims, under 35 U.S.C. 119(e), the benefit of a U.S. provisional application, Ser. No. 60/038,593 filed Mar. 5, 1997.

FIELD

The present invention relates to measuring and testing and, more particularly, to a method and apparatus for analyzing blood, particularly the coagulation characteristics of whole blood.

BACKGROUND

Coagulation is the process of clotting, and the phrase "time of coagulation" generally means the time required for a small amount of blood to coagulate. The time of coagulation indicates the propensity of blood to coagulate. It can be determined, and was for many years, by collecting blood in a small container and merely observing elapsed time from the moment the sample was obtained to the time it coagulated. Clearly, this method was not very precise. Coagulation time may also be determined by collecting blood in a small capillary tube, then breaking off short pieces of the tube until threads of fibrin appear between the broken ends. Precision may still be questionable, but coagulation time measured by the latter method is normally six to seventeen minutes.

More precise analyzer technologies that are currently available in hospitals for the assessing coagulation condition are typically found in the hospitals' central laboratories. These analyzers: (1) are usually complex and difficult to operate, requiring trained laboratory technicians; (2) are usually bulky in size and weight; and (3) have moving mechanical parts. Another disadvantage of many available instruments and methods of analysis of whole blood coagulation parameters is that they require separation of plasma from the test sample prior to analysis. As a result, currently available instruments and methods, particularly those used by hospitals in their central laboratories, are not well suited for point of care analysis of whole blood coagulation parameters. Point of care equipment should be (1) compact; (2) simple enough for operation by nurses or even lay persons; and (3) rugged enough to withstand the rigors of transport from bedside to bedside and use in emergency situations.

U.S. Pat. No. 5,580,744 (Zweig) and U.S. Pat. No. 5,418,141 (Zweig et al.) disclose a test article and method for determining coagulation capability in a blood sample. The test article is a porous membrane having a coagulation initiator and substrate impregnated therein. In use, blood is applied to one face of the membrane and plasma is absorbed into the interior of the membrane in the presence of the coagulation initiator and substrate. The membrane produces a detectable signal (i.e., a fluorescent signal) for reading by an automated detector or test system including a timer and means for calculating a coagulation value. Although the disclosed test article is said to be suitable for use in a home setting, as alluded to above, the Zweig test article requires that the plasma be separated from the sample.

U.S. Pat. No. 4,547,735 (Kiesewetter et al.) discloses another example of known apparatus and methods for measuring and testing blood. The disclosed instrument includes two electrodes with which the conductivity of a sample may be measured. The sample contacting faces of the electrodes are placed in vertically separated horizontal planes in an accurately fixed spacing so a blood column of a given size is formed from a sample. Current acts on the sample and the instrument measures change in impedance to determine the hematocrit value of blood. There is no suggestion that the instrument could be used to assess other characteristics or qualities of blood. The instrument is expressly designed to ignore or avoid the effect of sedimenting or aggregating.

U.S. Pat. No. 5,601,995 (Exner) discloses an apparatus and method for detecting coagulation. The method includes providing a porous sheet and applying a blood sample to the sheet so that the blood spreads through a part of the sheet. The spreading extent or spreading rate of the blood in the sheet is visualized, or measured by measuring electrical conductivity across the sheet, electrical potential across the sheet or an electrical resistance of the sheet. In the visual or optical embodiment, one measures the extent of area covered by the sample prior to coagulation, or the rate of growth of the area of the spread sample and tries to extrapolate the time of coagulation from those observations. In the conductivity embodiment, electrodes are provided on either side of the porous sheet. The conductivity or electrical impedance between the electrodes depends on the wetted area between them and, as a sample spreads through the porous sheet, impedance is reduced and conductivity increased, thereby indicating the extent of spread in the sheet. In theory, coagulation has occurred when the rate of change in conductivity/impedance approaches zero. Obviously, in the visual or optical embodiment, one problem is that mere visual observation may not be very accurate. In either embodiment, the porous sheet may be affected by ambient conditions and handling, particularly severe problems if point of care use is attempted.

U.S. Pat. No. 5,298,224 (Plum) and U.S. Pat. No. 5,167,145 (Butler et al.) disclose apparatus for determining blood coagulation time using optical means. The Plum patent discloses the use of light and light detectors to measure blood transillumination and to determine coagulation time. The Butler et al. patent discloses the use of an infrared source and a photo detector to measure electromagnetic transmission and to determine coagulation time.

While the preceding patents reveal advances in the art of evaluating coagulation parameters or characteristics of blood, none discloses or provides an optimally durable, simple, portable and reliable apparatus and method for point of care use. Accordingly, there exists a need for such an analyzer and a method of analysis for accurately and reliably measuring coagulation characteristics of whole blood.

SUMMARY

The present invention provides a method of assessing the coagulation characteristics of blood. The method involves assessing a condition in a portion of a blood sample and relating the condition to the onset of coagulation. Apparatus for performing the method is encompassed.

In one embodiment, the apparatus includes an electrochemical cell wherein electrodes are positioned in close proximity at the bottom of the cell to make coagulation time measurements of a whole blood sample by measuring electrochemical resistance between the electrodes. By measuring the bottom fraction of the blood, the apparatus detects only resistance changes in the red blood cell fractions and, thus, measures resistance increases caused by the increase in number of red blood cells settling into the area of the electrical field as a function of time. By determining when resistance stops increasing, the onset of coagulation is determined and coagulation time can be determined and/or predicted.

In another embodiment, optically based measurements of the coagulation parameters are made by utilizing a wavelength that is absorbed by red blood cells. A light beam is positioned in an optical path into which red blood cells settle as a function of time. By determining when the light beam wavelength absorption stops increasing, the onset of coagulation is detected.

A clotting reagent may be introduced into a disposable electrochemical or optical cartridge or sample container by incorporating the reagent in the test fluid flow path where they are dissolved into the blood as the sample is introduced into the cartridge. In another embodiment, the reagent may be contained in the sensor (and/or electrode) or light path chamber in a dried form and then dissolved into the sample with blood introduction.

An advantage of such a portable analysis system is that it could be used in hospital settings to characterize patient condition before, during, and after operations where control of coagulation condition is vital to a successful outcome. Another advantage is that this system could be used in out patient settings, to evaluate patients on anti-coagulant therapies, such as treatment with Warfarin.

Other features and advantages of the present invention will become more fully apparent and understood with reference to the following description and to the appended drawings and claims.

DESCRIPTION

The present invention encompasses a method and apparatus to make coagulation time measurements of a whole blood sample, without separating out the plasma fraction, using an instrument with no moving mechanical parts.

The term "electrochemical cell" is intended to mean a sample material on which electricity acts and at least two electrodes operably coupled to the sample material for communicating electricity to the sample material. Suitable circuit means (wiring, integrated circuits, power source and the like) and control means (a microprocessor, CPU or the like and related software) may be operably incorporated with the cell. As used herein and in the art generally, the term "sensor(s)" is intended to encompass an electrode(s) or a combination of electrodes for analyte measurements, and is intended to be used interchangeably with electrode(s) in any electrochemical embodiment of the present invention. With regard to means for fastening, mounting, attaching or connecting the components of the present invention to form the analyzing device as a whole, unless specifically described as otherwise, such means are intended to encompass conventional connecting mechanisms. Unless specifically otherwise disclosed or taught, materials for making the components of the present invention may be selected from appropriate materials such as metal, metallic alloys, various plastics and the like.

One example of a component device suitable for use in practicing the electrochemical embodiment of the present invention is the IRMA® device manufactured and sold by Diametrics Medical, Inc. of Minneapolis, Minn. To use the IRMA® device, a sample cartridge suitable for use with the IRMA® device is provided for receiving a sample. The cartridge includes two closely spaced electrodes, approximately 0.003 inches apart, in the device's cartridge blood flow path. The two electrodes are electrically coupled to the IRMA® device which is programmed to provide a selected current across the electrodes and to measure, record and process a change in resistance. The device may be adapted to assess or monitor resistance and relate a change in resistance to the onset of coagulation, and to provide a time readout (i.e., a coagulation time readout) to an operator. Optionally, other sensors may be situated in the blood flow channel or path for concurrent or separate measurement of other analytes, such as oxygen, carbon dioxide, pH, hematocrit, calcium, potassium, sodium chloride, urea, creatinine or glucose.

Figure 3:
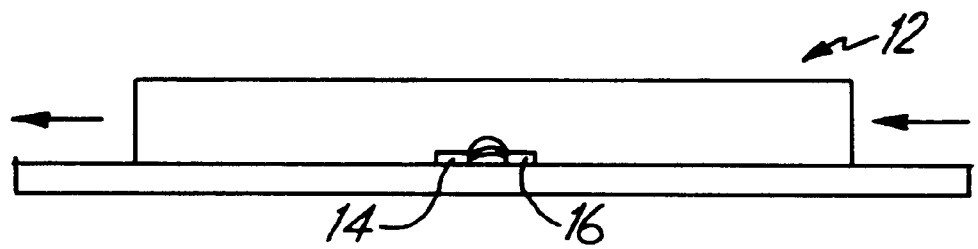
FIG. 3 is a side view of a blood sample chamber that includes two closely spaced electrodes that create an electrical field limited to the bottom area of the sample chamber.
Figure 5:
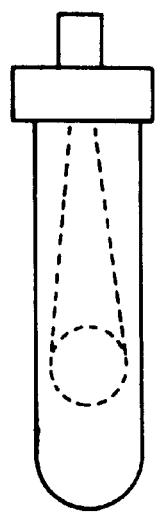
FIG. 5 is a front view of an exemplary optical cell for use in performing an embodiment of the method of the present invention.

In the following description, any references to right and left, top and bottom, upper and lower and horizontal and vertical are to be read and understood with reference to viewing the embodiment of the analyzing unit of the present invention as shown in FIGS. 3 and 5. Elements or components common to depicted embodiments of the present invention are commonly numbered.

Figure 1:
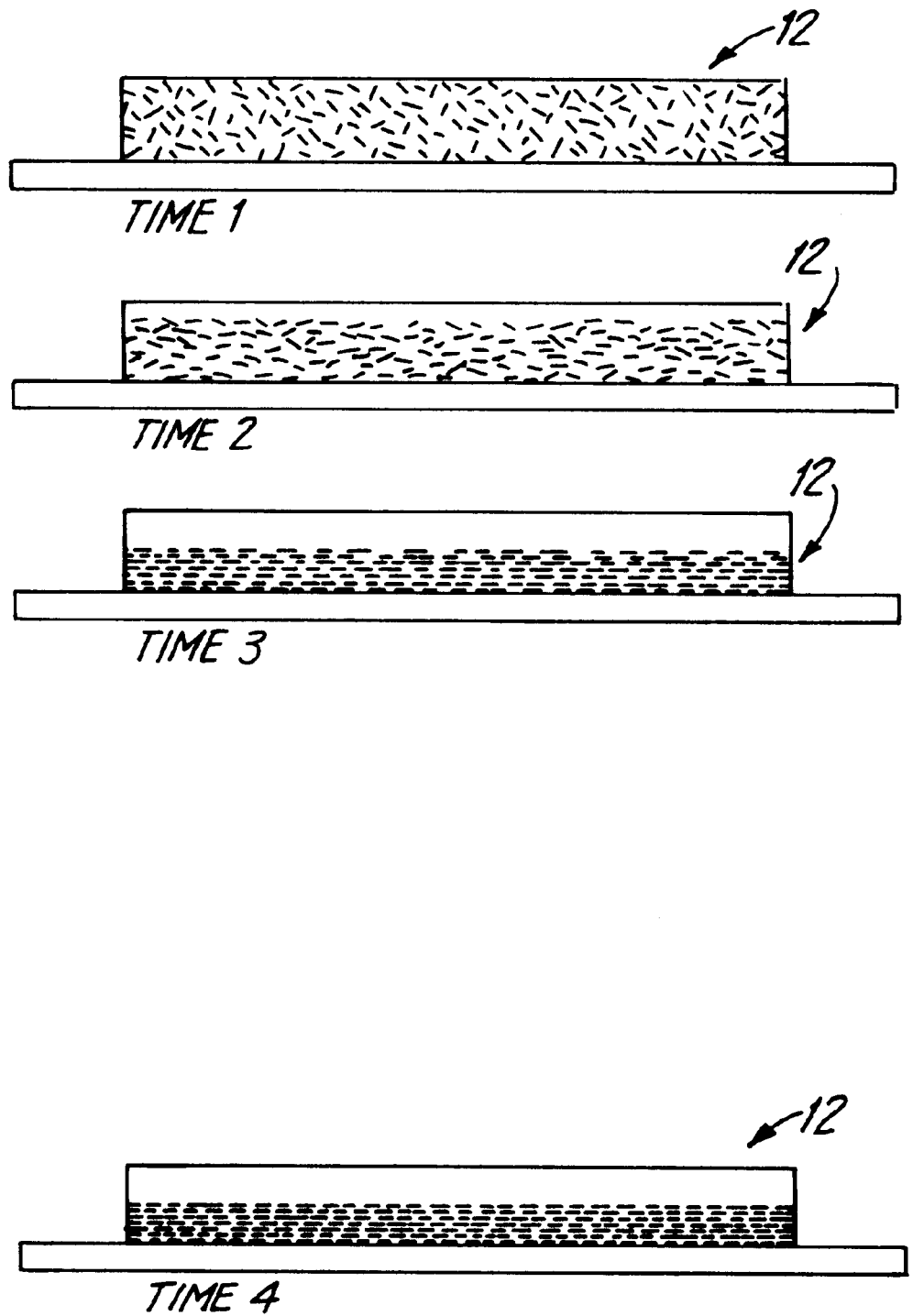
FIG. 1 represents blood held in an exemplary sample chamber or container and illustrates the settling of red blood cells in that chamber or container at four different time intervals.

It is well known that the red blood cells in whole blood will settle as a function of time when held in a container 12, as illustrated in FIG. 1. At time 1, the cells are dispersed, at times 2 and 3 settling and, at time 4, settled at or near the bottom of the container. The settling process naturally ceases upon the onset of coagulation. The present invention uses this phenomenon to measure the time it takes for the onset of coagulation. In one embodiment, the present invention take advantage of the fact that resistance between two electrodes in a blood sample is related to the concentration of red blood cells in that sample.

Figure 2:
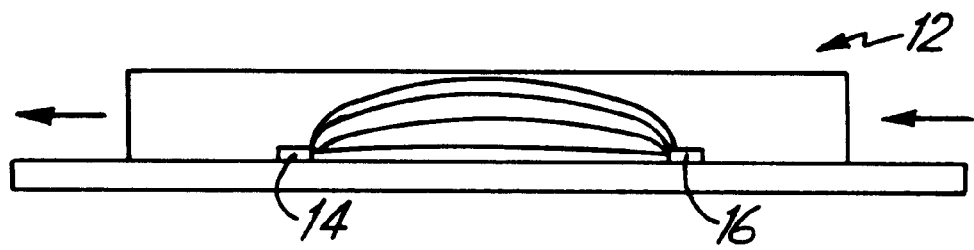
FIG. 2 is a side view of a blood sample chamber that includes two spaced electrodes that create an electrical field that reaches the top of the sample chamber.

Referring to FIG. 2, past attempts to measure coagulation time by electrochemical resistance methods have generally not been as accurate as desired, at least in part because the methods are not specific enough to adequately relate a resistance change to coagulation time. The primary reason is that such methods used electrodes 14, 16 widely spaced from each other, thus measuring total cell resistance as shown in FIG. 2. Measuring total cell resistance does not accurately detect resistance changes associated with blood settling, because it does not discriminate between low resistance and high resistance red blood cell fractions or location in the sample chamber.

Figure 4:
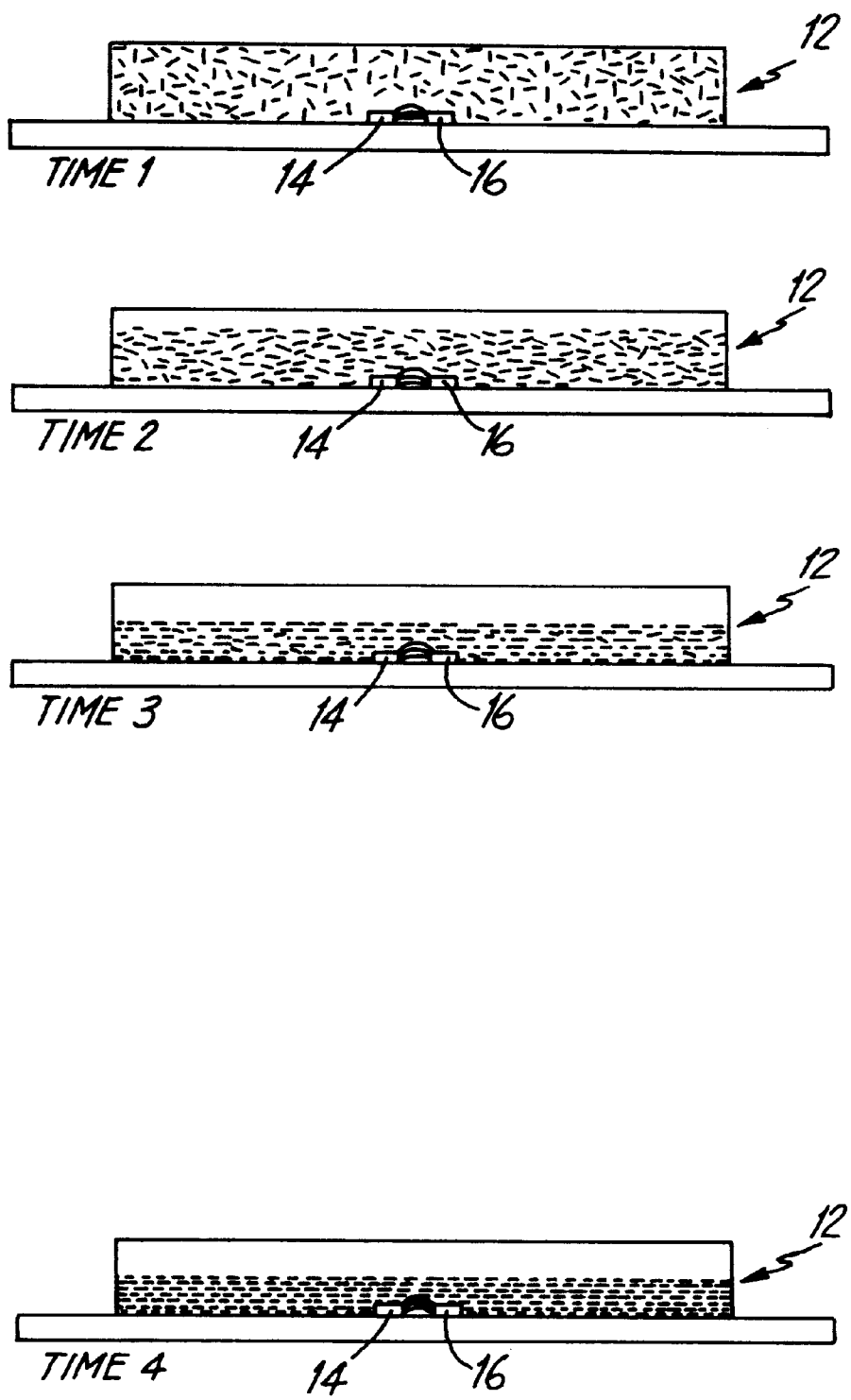
FIG. 4 represents blood held in a sample chamber that includes two closely spaced electrodes and illustrates the relationship of the electrical field to the settling of red blood cells in the chamber at four different time intervals.

Referring to FIGS. 3 and 4, in the apparatus of the present invention the electrodes 14, 16 are positioned close together, in one embodiment approximately 0.003 inches apart, at the bottom of an electrochemical cell or sample chamber 12. The electrical field is thus substantially limited to the bottom fraction of the blood sample and the apparatus detects only resistance changes in the red blood cell fractions and, thus, more accurately measures the resistance increase caused by the increase in number of red blood cells settling into the area of the electrical field as a function of time. By adding a clotting reagent (hereinafter "reagent") to a whole blood sample and determining when resistance stops increasing, the onset of coagulation is detected. This process is visually represented in FIG. 3. Red blood cell settling effects have been assessed or quantified using a planar electrode arrangement, utilizing gold or like, generally coplanar electrodes spaced approximately 0.003 inches apart in a cell of 0.025 inch height, using an impedance measurement mode on a typical electrochemical cell or analyzer. While a 0.003 space between electrodes is used in one embodiment, the space may range approximately between 0.0001 and 0.0500 of an inch apart, and may be optimized according to the selected size of the sample containing chamber.

Figure 6:
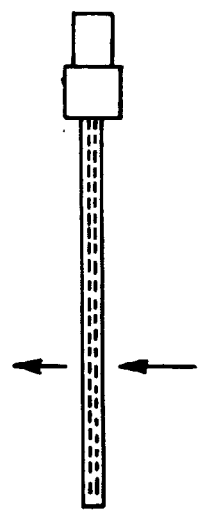
FIG. 6 is a side view of the optical cell depicted in FIG. 5.
Figure 7:
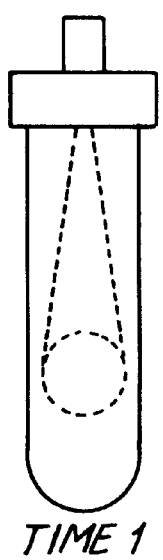
FIG. 7 represents blood held in the optical cell and illustrates the settling of red blood cells in the chamber at three different time intervals.
Figure 7:
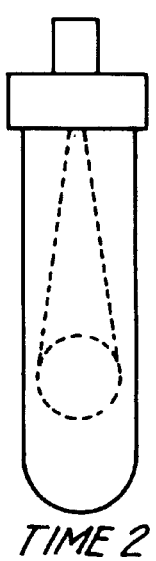
Figure 7:
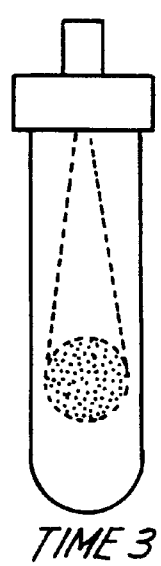

The method of the present invention, assessing a condition in a region or portion of a sample to quantify or characterize another condition or characteristic of the whole sample, may be adapted to use optically based measurements. For example, using a light source which generates a wavelength that is absorbed by red blood cells, and positioning the light beam from the source in an optical path into which red blood cells settle as a function of time, it can be determined when the settling of red blood cells ceases, i.e., when the change in absorption slows or stops, the lapsed time may be related to the onset of coagulation. FIGS. 5 and 6 depict an exemplary optical cell. FIG. 7 illustrates the optical path and changes that occur as the red blood cells of a whole blood sample settle.

Figure 8:
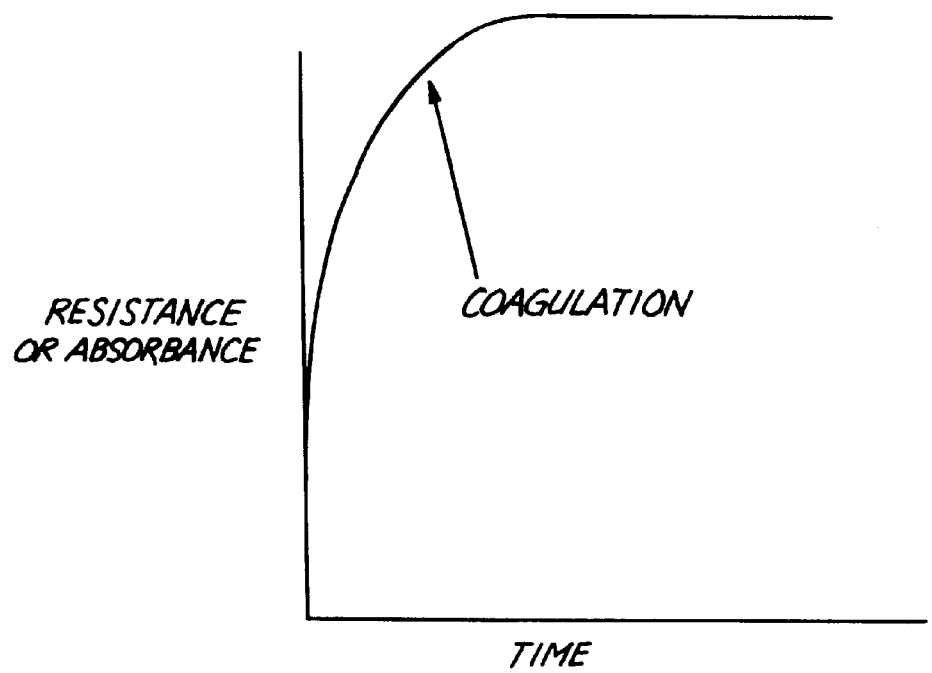
FIG. 8 is a graph of the change in electrical resistance or light absorbance over time as blood coagulates.
Figure 9:
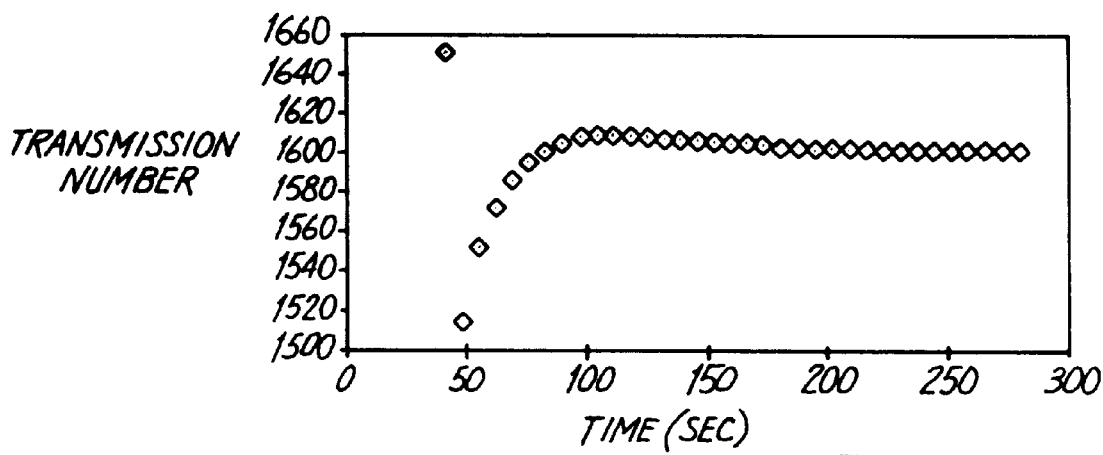
FIG. 9 depicts exemplary, experimentally derived results using the optical based coagulation detection method of the present invention.

FIG. 8 graphically illustrates how changes in resistance or absorbance can be related to coagulation and FIG. 9 presents exemplary, experimentally derived results using the optical based detection method.

Figure 10:
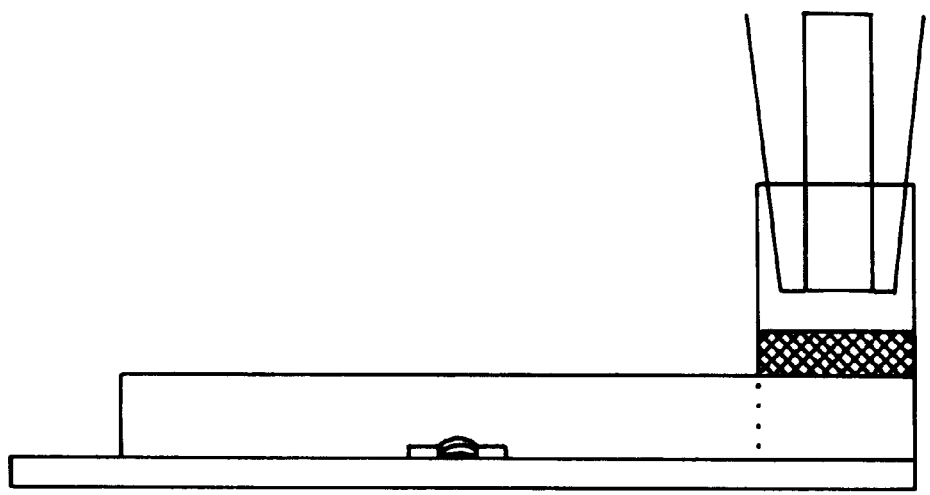
FIG. 10 depicts an exemplary mixing chamber for use with an electrochemical cell.
Figure 11:
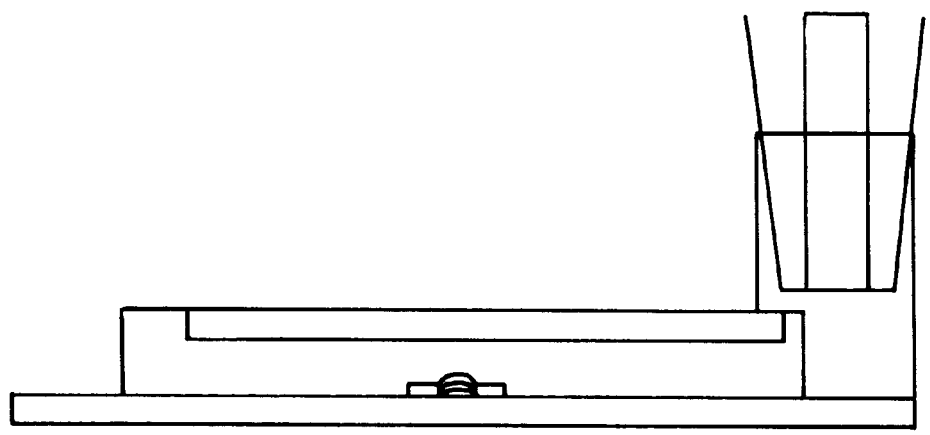
FIG. 11 depicts an exemplary coated reagent sample container for use with an electrochemical cell.
Figure 12:
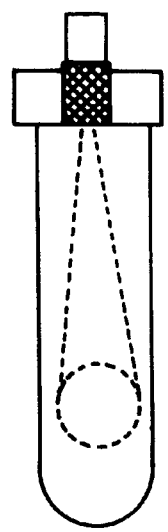
FIG. 12 depicts an exemplary mixing chamber for use with an optical cell.
Figure 13:
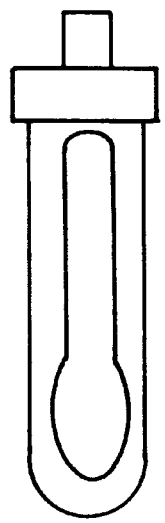
FIG. 13 depicts an exemplary coated reagent sample chamber for use with an optical cell.
Figure 13:

A suitable reagent (e.g., prothrombin, thrombin, thromboplatin, calcium, fibrogen or the like), which may be necessary for most coagulation measurements, can be introduced into a disposable electrochemical or optical cartridge by incorporating them in the fluid flow path, where they are dissolved into the blood as the sample is introduced into the cartridge. Examples of reagent mixing methodologies are represented in FIGS. 10 and 11 for electrochemical cells, and in FIGS. 12 and 13 for optical cells. In one method (FIGS. 10 and 12), the reagent is introduced via a premixing chamber prior to blood passing over the electrodes or into the light path. In another method (FIGS. 11 and 13), the reagent is contained in the electrode or light path chamber in a dried form, then dissolved into the sample with blood introduction. The reagents should be dissolved into the blood sample completely and quickly, so that reagent dissolution time will not adversely impact clotting time. For example, freeze drying reagents directly in an optical cell of 100 micron thickness, 1.8 cm width, and 5 cm height adequately served to enable measurement of red blood cell settling and coagulation onset, using a conventional laboratory spectrophotometer.

Reagents and their concentrations used are those typically associated with clotting measurements. For example, in the optical cell described above, a reagent deposit of thromboplastin and calcium can be used to determine the prothrombin time coagulation measurement.

Additionally, titration type measurements can be made using multiple cuvettes, or a single cuvette with multiple path chambers. For example, to characterize the heparin concentration of a blood sample, several cells of varying protamine concentration can be used to measure coagulation response to varying protamine doses. Thus, the protamine dosage to be administered to a patient can be quickly and easily determined.

Although a description of the invention has been presented, various embodiments, including those mentioned above, could be made or performed without deviating from the spirit of the present invention. It is desired, therefore, that reference be made to the appended claims rather than to the foregoing description to indicate the scope of the invention.

What is claimed is:

1. A method of assessing the coagulation propensity of blood comprising the steps of:

providing a blood sample;

assessing a condition in a portion of the blood sample, wherein the condition is the concentration of red blood cells in the portion; and relating the condition to the coagulation propensity of the blood sample.

2. The method according to claim 1, wherein the concentration is related to the settling of red blood cells into the portion.

3. The method according to claim 2, further comprising relating the time it takes said settling to cease to the onset of coagulation.

4. A method of optically measuring coagulation time of a blood sample which comprises the steps of directing a light beam into an optical path into which red blood cells settle over time and relating the time it takes said settling to occur to the onset of coagulation.

* * * * *